United States Patent [19]

Schöb et al.

[11] Patent Number: 5,454,822
[45] Date of Patent: Oct. 3, 1995

[54] APPARATUS FOR CLAMPING AND CUTTING VISCERA

[75] Inventors: Othmar Schöb, Urdorf; Max Spillman, Rudolfstetten, both of Switzerland

[73] Assignee: K. Widmann AG, Rudolfstetten, Switzerland

[21] Appl. No.: 171,611

[22] Filed: Dec. 22, 1993

[30] Foreign Application Priority Data

Dec. 31, 1992 [CH] Switzerland ............................ 3997/92
Aug. 5, 1993 [CH] Switzerland ............................ 2340/93

[51] Int. Cl.⁶ .................................................. A61B 17/00
[52] U.S. Cl. ........................ 606/148; 606/144; 606/167; 606/170; 606/207; 112/169
[58] Field of Search ...................................... 606/174, 167, 606/170, 147, 145, 144, 148, 139, 1, 205–208; 112/80.03, 169

[56] References Cited

U.S. PATENT DOCUMENTS

| | | | |
|---|---|---|---|
| 3,470,875 | 10/1969 | Johnson | 606/145 |
| 3,807,407 | 4/1974 | Schweizer | 606/145 |
| 4,493,323 | 1/1985 | Albright et al. | |
| 4,935,027 | 6/1990 | Yoon | |
| 5,037,433 | 8/1991 | Wilk et al. | 606/144 |
| 5,147,373 | 9/1992 | Ferzli | 606/144 |
| 5,188,636 | 2/1993 | Fedotov | 606/144 |
| 5,261,917 | 11/1993 | Hasson et al. | 606/148 |
| 5,342,389 | 8/1994 | Haber et al. | 606/148 |

FOREIGN PATENT DOCUMENTS

| | | |
|---|---|---|
| 0332591 | 9/1989 | European Pat. Off. |
| 0369324 | 5/1990 | European Pat. Off. |
| 2081099 | 2/1982 | United Kingdom |

*Primary Examiner*—Stephen C. Pellegrino
*Assistant Examiner*—Jeffrey A. Schmidt
*Attorney, Agent, or Firm*—Martin A. Farber

[57] ABSTRACT

An apparatus for clamping and cutting viscera in abdominal or thoracic cavities has an elongated tubular support for two toothed jaws which are pivoted to one end of the support. The latter can receive a prefabricated carriage with two needles and a length of thread connected to the rear ends of the needles. A sleeve is employed to close the jaws or to permit the jaws to open under spring bias, and a handle is provided to move a piston which is reciprocable in the support to expel the needles from the carriage, through a plug at the front end of the support and through channels in the jaws whose teeth define a zig-zag shaped clearance for a selected portion of a viscus. The needles are thereupon extracted from the jaws into a body cavity whereby the thread forms stitches which connect mutually inclined parts of the clamped portion of a viscus to each other before the needles are detached from and the thread is tightened around the selected portion of the viscus. A cutter can be detachably affixed to the piston to automatically sever the viscus at a desired distance from the clamped portion.

31 Claims, 5 Drawing Sheets

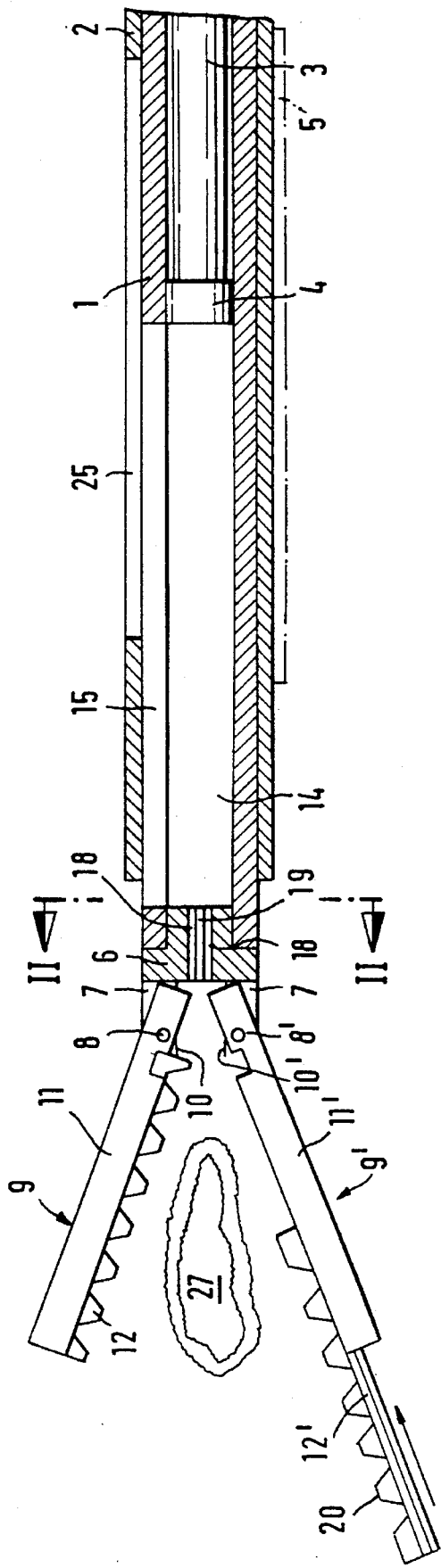

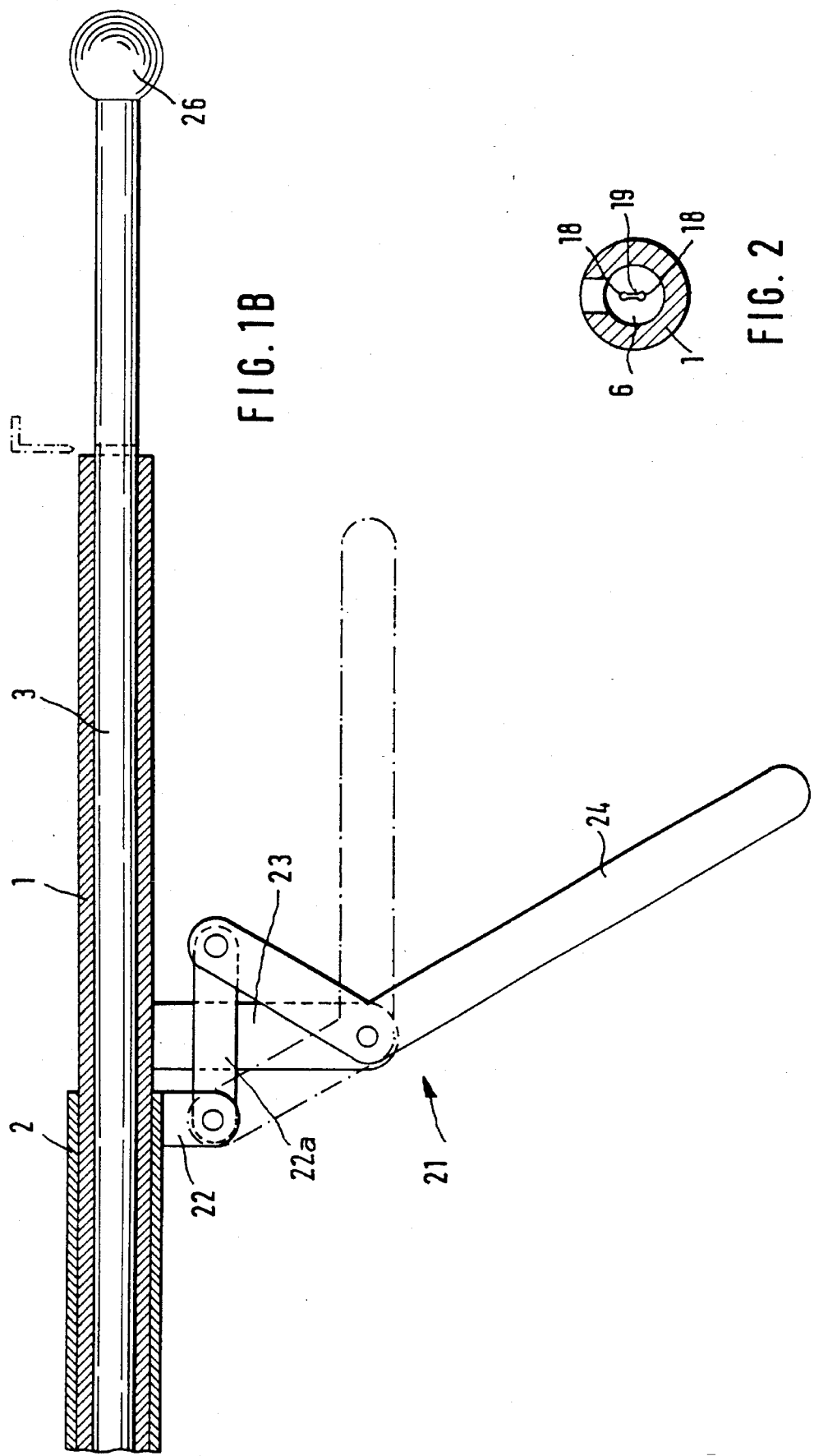

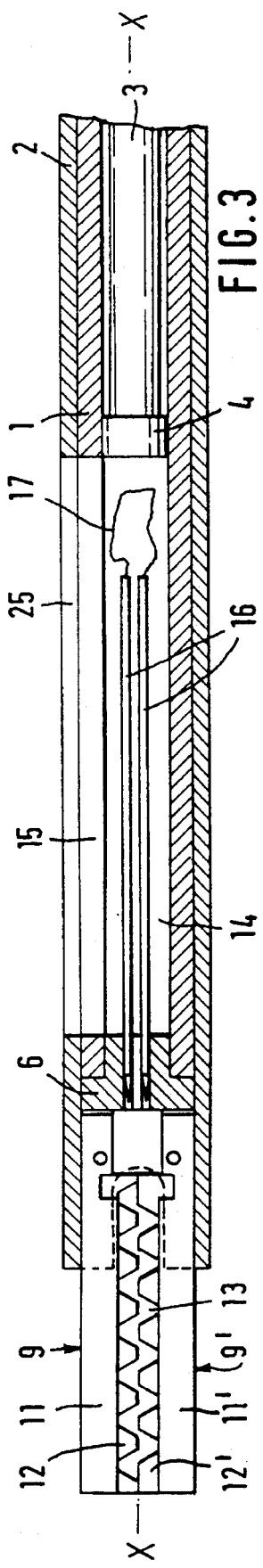
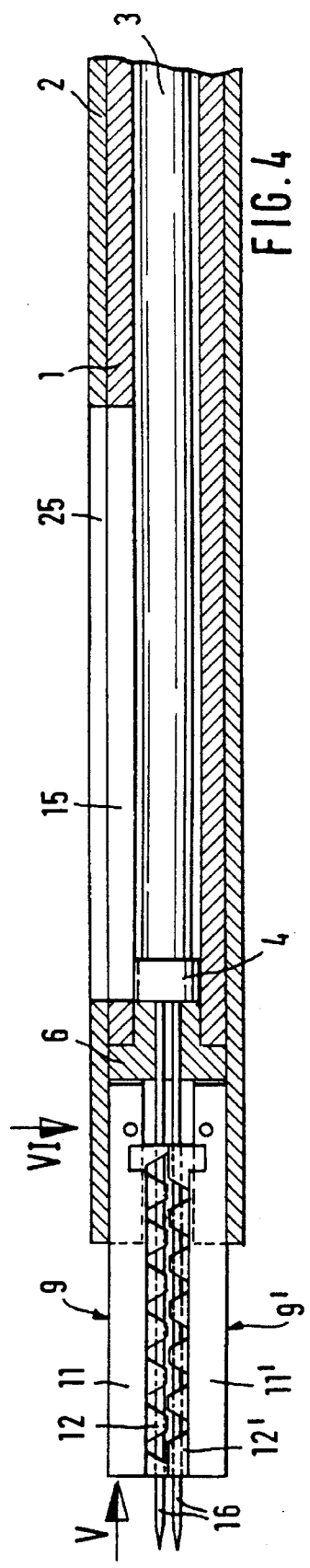
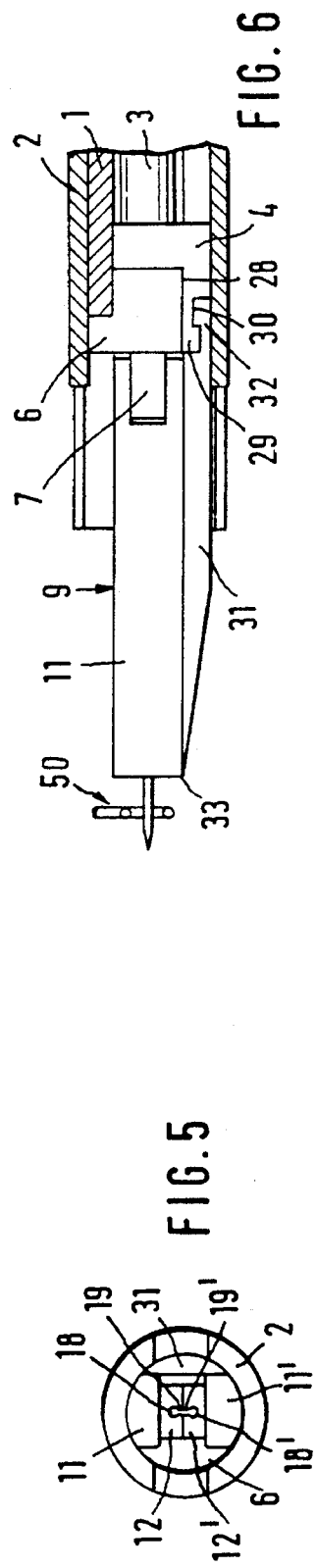

APPARATUS FOR CLAMPING AND CUTTING VISCERA

BACKGROUND OF THE INVENTION

The present invention relates to surgical implements in general, and more particularly to improvements in apparatus for clamping, sewing and cutting or trimming organs of living bodies, particularly viscera in abdominal or thoracic cavities.

It is known to employ a surgical apparatus to provide a severed viscus with a closure not unlike that known from old-fashioned tobacco pouches. Such apparatus or instruments are used upon opening of the abdominal or thoracic cavity to clamp a viscus for the purpose of introducing a thread which is thereupon tightened around a selected portion of the viscus in imitation of the thread or string at the openable end of a tobacco pouch. Anastomosis is but one of numerous surgical procedures which can be carried out by utilizing a clamping apparatus at the open end or at the open portion of an internal organ. Another procedure which can be carried out with a clamping and sewing apparatus is resection of viscera.

A drawback of presently known apparatus for the above outlined purposes is that their application and utilization take up an inordinately large amount of time. Certain conventional apparatus employ a pair of needles which must be individually introduced into and pushed along guides. The next step involves tightening of the thread which is affixed to the needles so that the tightened thread closes the open part of a viscus in a manner known for the openable end of a pouch. Though the clamping means of conventional apparatus simplify the task of a surgeon, the utilization of such instruments still necessitates the expenditure of a considerable amount of time and much skill.

Another drawback of conventional apparatus of the above outlined character is that they are rather bulky and expensive. Furthermore, certain mobile constituents of conventional apparatus cannot be reliably maintained in optimum positions preparatory to, during and subsequent to introduction into a body cavity, e.g., through a standard trocar. Moreover, it is not possible to immediately and reliably ascertain the momentary position of each movable constituent. Accordingly, there exists an urgent need for simple, versatile, compact and relatively simple apparatus which can be utilized by surgeons to close the open ends or severed parts of internal organs, particularly viscera in abdominal and/or thoracic cavities.

OBJECTS OF THE INVENTION

An object of the invention is to provide an apparatus which can be put to use to rapidly clamp and seal a viscus and which comprises a small number of simple parts.

Another object of the invention is to provide an apparatus which can seal a viscus not unlike a tobacco pouch at a selected distance from a cut in the clamped organ.

A further object of the invention is to provide the apparatus with novel and improved means for severing viscera in abdominal or thoracic cavities of human or animal bodies.

An additional object of the invention is to provide an apparatus which can be utilized by surgeons to perform laparotomic surgery.

Still another object of the invention is to provide a surgical implement which can be utilized in conjunction with a conventional trocar.

A further object of the invention is to provide an apparatus which can direct a thread against a selected portion of an organ in a body cavity with a high degree of accuracy.

Another object of the invention is to provide an apparatus which can be readily converted for the treatment of different viscera.

An additional object of the invention is to provide an apparatus which can be used for resection of internal organs.

Still another object of the invention is to provide novel and improved means for moving, positioning and arresting certain mobile parts of the above outlined apparatus.

A further object of the invention is to provide a novel and improved method of manipulating the above outlined apparatus.

Another object of the invention is to provide a novel and improved container for introduction of needles into an apparatus of the above outlined character.

An additional object of the invention is to provide a novel and improved cutter or knife for use in the above outlined apparatus.

Still another object of the invention is to provide an apparatus which can be utilized to perform its intended functions within shorter intervals of time than heretofore known apparatus.

SUMMARY OF THE INVENTION

One feature of the present invention resides in the provision of a surgical apparatus for clamping and sealing a viscus in a body cavity (such as the abdominal or thoracic cavity). The improved apparatus comprises a support having a front end which is insertable into a body cavity (e.g., through a trocar), a rear end and a compartment which is disposed between the two ends and serves to receive two needles having rear portions connected to each other by a length of flexible material and front portions. The apparatus further comprises two jaws which are affixed to and are movable relative to the front end of the support between closed positions (in which a viscus is to be clamped between the closed jaws) and open positions. The jaws have channels each of which is positioned to receive one of the two needles in response to expulsion of the needles from the compartment while the jaws are closed, and the apparatus also comprises means for moving the needles from the compartment into and beyond the channels so that the needles entrain the flexible material from the compartment and through the viscus between the closed jaws.

The flexible material can include a length of thread, and the channels preferably communicate with each other in the closed positions of the jaws so that a looped portion of the thread between the rear portions of the needles can be tightened against a viscus between the closed jaws in response to movement of the needles beyond the channels, i.e., into a body cavity.

The support can include or constitute an elongated straight tube, and the compartment can be disposed in the tube at the front end of such support. The tube can be provided with an elongated lateral inlet (e.g., in the form of an elongated axially parallel slot) for introduction of a pair of needles into the compartment. The moving means of such apparatus can include a piston which is reciprocable in the tube toward and away from the front end of the support to expel the needles from the compartment into the channels in response to movement toward the front end of the support while the jaws are closed. The piston is movable away from the front end toward the rear end of the support to assume a position behind or beyond the compartment so that the compartment is free to receive a pair of needles.

The jaws can be substantial mirror images of each other with reference to a plane including the central longitudinal axis of the tube. The channels of such jaws are parallel to the axis of the tube when the jaws are caused to assume their closed positions. The front end of the support can be defined by a stopper or plug having interconnected centering passages which are aligned with the channels and communicatively connect the channels with the compartment in the closed positions of the jaws. The passages can constitute holes or bores in the front end of the support, and such front end is preferably provided with a slot between the two passages.

In accordance with a presently preferred embodiment, the jaws are pivotable relative to the front end of the support about at least substantially parallel axes which are or which can be at least substantially normal to the longitudinal axis of the aforementioned tube. The external surface of the tube forming part of or constituting the support can be at least substantially flush with the external surfaces of the jaws when the jaws are held in their closed positions. This renders it possible to employ a sleeve which surrounds a portion of the support and is movable in the direction of the longitudinal axis of the tube between a first position in which the sleeve surrounds at least a portion of each jaw to maintain the jaws in closed positions, and a second position in which the jaws are free to pivot relative to the front end of the support toward and from their open positions.

The apparatus can comprise means (e.g., in the form of torsion springs) for yieldably biasing the jaws to their open positions. Thus, the jaws assume their open positions as soon as the sleeve is moved away from the first position to an extent which is necessary to enable the biasing means to pivot the jaws from the closed positions.

As already mentioned above, the tube of the support can be provided with an inlet for introduction of needles (or of a specially designed carriage for needles) into the compartment of the support. The sleeve can be provided with a second inlet which registers with the inlet of the tube at least in the first position of the sleeve. This ensures that the sleeve does not interfere with the introduction of needles into the compartment.

The tube of the support can be said to constitute an elongated cylinder for the aforementioned piston of the moving means. Such piston is preferably provided with an elongated piston rod which extends from the cylinder beyond the rear end of the support. The moving means can further comprise a handle (e.g., in the form of a substantially spherical knob) on the piston rod externally of the cylinder.

The support can carry a suitable linkage which is operatively connected with the sleeve and is actuatable to move the sleeve between the aforementioned first and second positions.

The outer diameter of the sleeve is preferably less than 19 millimeters; this facilitates convenient manipulation of the apparatus at the exterior of a body cavity as well as when the jaws are being introduced into a cavity to clamp a selected portion of a viscus.

The jaws can be provided with confronting teeth which define a substantially zig-zag shaped clearance in the closed positions of the jaws; such clearance can receive a selected portion of a viscus. Each jaw can be designed to have a first portion which is movably affixed to the support, and a second portion which is engageable with a viscus and is preferably detachably carried by the respective first portion. For example, the first portion of each jaw can include an elongated rail, and the second portion of each jaw can include an elongated toothed matrix which is releasably secured to the respective rail.

Still further, the apparatus can comprise a cutter or knife which is substantially parallel with the jaws in the closed positions of the jaws and is movable relative to the closed jaws to sever a viscus which is being clamped by the jaws. Such apparatus can further comprise means for preferably releasably (detachably) coupling the cutter with the moving means so that the cutter is moved relative to the closed jaws in response to movement of the needles from the compartment into and beyond the channels of the respective closed jaws. If the moving means comprises the aforementioned reciprocable piston, the coupling means can include an extension which is provided on the piston, which projects toward the jaws, and which is connectable with a portion of the cutter. If the plug at the front end of the support is provided with interconnected passages which together form a slot and establish a path for movement of the needles from the compartment into the passages in closed positions of the needles, the extension can project beyond and is then adjacent the passages in response to movement of the needles at least partially beyond the channels.

The moving means can further comprise means for extracting the needles from the channels into a body cavity in closed positions of the jaws. The needles are or can be made of a ductile material, and the extracting means can be designed to convert the needles into spirals in response to extraction from the respective channels in a direction away from the support. The extracting means can resemble a sardine can opener.

Another feature of the invention resides in the provision of a novel article of manufacture for use with a surgical apparatus of the above outlined character. The novel article comprises a cutter or knife having a portion connectable with the moving means so that it can move relative to and between the sleeve on the one hand and the jaws on the other hand while the jaws are maintained in closed positions and while the sleeve assumes a predetermined position corresponding to the aforementioned first position in which the sleeve at least partially surrounds the closed jaws.

An additional feature of the invention resides in the provision of a novel article of manufacture which can be utilized in the above outlined apparatus and includes an elongated carriage (which can have a square, rectangular or other polygonal cross-sectional outline). The carriage is insertable into and is withdrawable from the compartment of the support and has an external surface provided with two longitudinally extending needle-confining grooves. The carriage is preferably further provided with two longitudinally extending thread-receiving channels each of which communicates with one of the grooves, and such carriage is also provided with at least one longitudinally extending thread-receiving chamber having at least one open end. The carriage has a first end and a second end and can be provided with a recess which is disposed at one end of the carriage and communicates with the adjacent ends of the longitudinally extending grooves and channels in the carriage. Such carriage can be further provided with a cutout at one or both ends, and the at least one open end of the chamber or chambers in the carriage can communicate with such cutout. The two ends of the carriage can be mirror images of each other.

The novel features which are considered as characteristic of the invention are set forth in particular in the appended claims. The improved surgical apparatus itself, however, both as to its construction and its mode of operation, together with additional features and advantages thereof, will be best understood upon perusal of the following detailed description of certain presently preferred specific embodiments with reference to the accompanying drawings.

BRIEF DESCRIPTION OF THE DRAWINGS

FIG. 1A is a fragmentary partly elevational and partly central longitudinal sectional view of the front part of an apparatus which embodies one form of the invention, the jaws being shown in open positions and a viscus being shown between the open jaws;

FIG. 1B is a fragmentary partly elevational and partly central longitudinal sectional view of the rear part of the apparatus which is shown in FIG. 1A;

FIG. 2 is a sectional view substantially as seen in the direction of arrows from the line II—II in FIG. 1A;

FIG. 3 illustrates the structure of FIG. 1A but with the jaws in closed positions;

FIG. 4 is a view similar to that of FIG. 3 but with the needles partially expelled from the channels in the respective jaws;

FIG. 5 is an end elevational view as seen in the direction of arrow V in FIG. 4;

FIG. 6 is a fragmentary partly central longitudinal sectional and partly elevational view of the apparatus, substantially as seen in the direction of arrow VI in FIG. 4;

DESCRIPTION OF PREFERRED EMBODIMENTS

Figure 7:
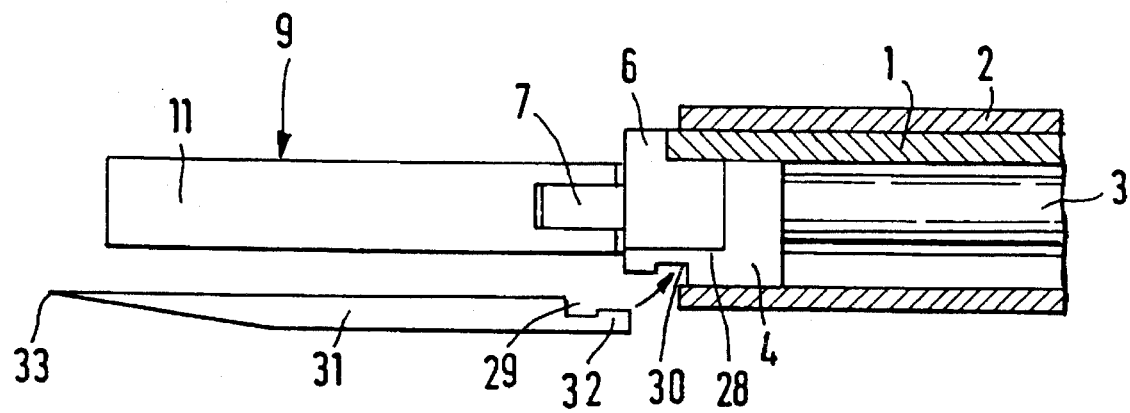
FIG. 7 is a view similar to that of FIG. 6 but with the cutter detached from the extension of the piston in the tube of the support.
Figure 8:
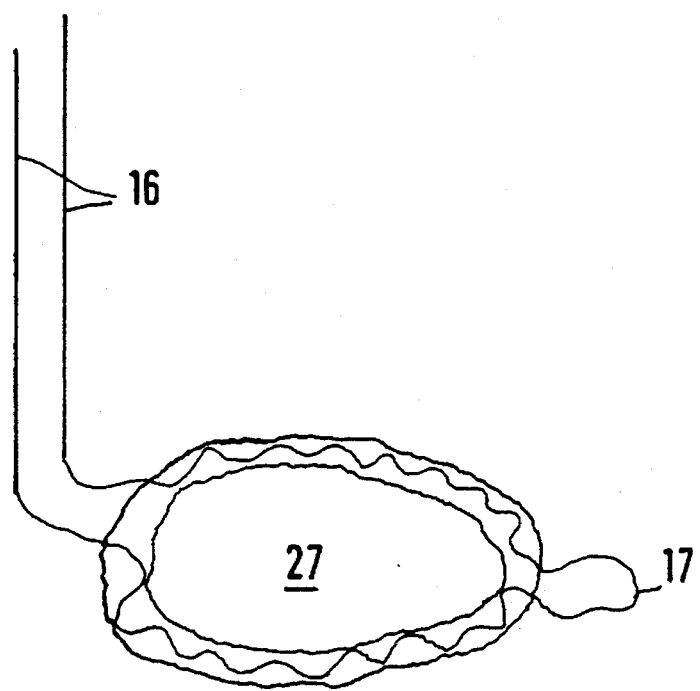
FIG. 8 illustrates the pouch-like closure at an open end of a viscus prior to tightening of the thread.

Referring first to FIGS. 1A to 5, there is shown a surgical clamping and sealing (tightening) apparatus for viscera in body cavities, e.g., for a severed viscus 27 (FIG. 1A) in an abdominal or thoracic cavity. The improved apparatus comprises an elongated support including a cylindrical tube 1 which is partially sealed by a specially designed stopper or plug 6 at the front end, and which is also sealed at its rear end. The front end of the tube 1 carries two pivotable jaws 9, 9' and the tube confines a reciprocable piston 4 forming part of a device for moving two elongated needles 16 from an elongated compartment 14 in the tube 1 through channels 18' defined by the jaws 9, 9' and partially into a body cavity which confines the viscus 27. The jaws 9, 9' are pivotable between the open positions (FIG. 1A) and closed positions (FIGS. 3 to 5), and the needles 16 can be expelled from the compartment 14 to enter the channels 18' when the jaws are caused to assume their closed positions.

The means for pivoting the jaws 9, 9' to their closed positions includes an elongated cylindrical member 2 (hereinafter called sleeve) which surrounds a portion of the tube 1 and is reciprocable between a first or extended position (FIGS. 3 to 5) in which the jaws are locked in the closed positions and a second or retracted position (FIGS. 1A and 1B) in which the jaws are free to pivot away from the closed positions toward the open positions or vice versa.

The sleeve is partially surrounded by a trough-shaped closure 5 (indicated in FIGS. 1A by phantom lines) which extends along an arc of at least 180° and can be turned by hand so as to overlie a selected portion of the external surface of the sleeve 2. The arrangement is preferably such that the internal surface of the closure 5 engages the external surface of the sleeve 2 with a certain amount of friction so as to ensure that the closure 5 will remain in a selected angular position unless intentionally moved to a different angular position.

The plug 6 of the support is disposed at the front end of and partially extends into and is affixed to the tube 1 to define the front end of the compartment 14. The cylindrical external surface of the larger-diameter front portion of the plug 6 is preferably flush with the cylindrical external surface of the tube 1 as well as with the external surfaces of the jaws 9, 9' provided that the jaws are maintained in the closed positions as shown in FIGS. 3, 4 and 5. This ensures that the sleeve 2 can be moved axially over and forwardly beyond the plug 6 in order to engage and pivot the jaws 9, 9' to their closed positions. The larger-diameter front portion of the plug 6 extends beyond the front end of the tube 1 and is provided with a diametrically extending slot 7 traversed by two bearing pins 8, 8' for the jaws 9 and 9', respectively. The axes of the bearing pins 8, 8' are parallel to each other and normal to the central longitudinal axis X—X of the tube 1.

The jaws 9 and 9' are permanently biased to the open positions of FIG. 1A by two torsion springs 10 which are convoluted around the respective bearing pins 8, 8' to react against the plug 6 and to bear against the adjacent parts of two elongated rails 11, 11' respectively. The rails 11, 11' constitute the first portions of the respective jaws 9, 9', and these jaws further respectively comprise toothed second portions or matrices 12, 12' which are adjustably and removably installed in the respective rails 11 and 11'. Each of the rails 11, 11' is preferably a rigid member which can have a substantially T-shaped or V-shaped cross-sectional outline to receive a portion of the respective matrix 12, 12'. The matrices 12, 12' have confronting toothed surfaces 20 which together define a zig-zag shaped space or clearance 13 when the jaws 9 and 9' assume their closed positions. In order to prevent the teeth of the matrix 12 from entering the tooth spaces between the teeth of the matrix 12', the two sets of teeth are offset relative to each other in the longitudinal direction of the respective jaws 9 and 9'. Furthermore the foremost and/or the rearmost tooth of the matrix 12 abuts the adjacent tooth of the matrix 12' to ensure that these matrices establish the aforementioned zig-zag shaped clearance 13 for a portion of a viscus 27 when the jaws 9, 9' are caused to move to their closed positions. The arrangement may be such that the matrices 12, 12' can be mounted in the respective rails 11, 11' by pushing them into the T-shaped or V-shaped grooves of the adjacent rails in a direction from the free ends of the rails toward the respective bearing pins 8, 8'. Instead of the illustrated form-locking connections between the rails 11, 11' and the respective matrices 12, 12', it is equally possible to establish force-locking connections and/ or to employ screws or other fasteners which can preferably releasably hold selected matrices of one of two or more pairs of matrices in optimum positions relative to each other.

FIG. 1A shows the matrix 12 in the fully inserted position and the matrix 12' in the process of advancing toward the fully inserted position of FIG. 3 or 4. Each of two or more sets or pairs of matrices 12, 12' can be provided with a row of differently dimensioned, configurated and/or distributed teeth, depending upon the nature of that portion of a viscus 27 which is to be clamped between the matrices 12, 12' in the closed positions of the jaws 9 and 9'.

The aforementioned compartment 14 constitutes an elongated portion of the internal space of the tube 1 adjacent the inner end of the plug 6 and is accessible through an elongated slot-shaped lateral inlet 15 of the tube. The sleeve 2 is provided with a second elongated inlet 25 which is caused to register with the inlet 15 (either entirely or at least in part) in response to axial movement of the sleeve 2 to the first position of FIG. 3 or 4. This renders it possible to insert a pair of needles 16 into the compartment 14 in such a way that the first or front ends or tips of the needles extend into the adjacent end portions of two passages 18 provided in the plug 6 behind the slot 7 for the bearing pins 8, 8' and the rearmost portions of the rails 11, 11'. The piston rod 3 of the piston 4 extends from the tube 1 (i.e., beyond the rear end of the tube) and is provided with a handle 26 (FIG. 1B shows a handle in the form of a substantially spherical knob) which can be manipulated by hand to move the piston 4 toward abutment with the plug 6 or in the opposite direction to an end position behind the compartment 14. The rear end portions of the needles 16 are connected to each other by a length of flexible material 17, preferably a thread, which can be caused to close a viscus 27 adjacent the open end of such organ in a manner to be fully described hereinafter.

The passages 18 in the rear portion of the plug 6 are two bores or holes which are parallel with the axis X—X of the tube 1 and such bores or holes communicate with each other by way of a diametrically extending slot 19 provided in the rear portion of the plug 6. The matrices 12, 12' of the jaws 9, 9' are provided with elongated channels 18' each of which is aligned with and communicates with one of the passages 18 when the jaws are caused to assume their closed positions. At such time, the passage 18' of the matrix 12 communicates with the passage 18' of the matrix 12' by way of a transversely extending elongated slot 19'. The purpose of the slots 19, 19' is to permit the passage of a looped portion of the thread 17 while the needles 16 are being extracted from the channels 18' into a body cavity.

The channels 18' and the slot 19' can be provided in the toothed surfaces 20 of the matrices 12 and 12'. When the top lands of teeth on one of the jaws 12, 12' are adjacent the top lands of teeth on the other matrix, the grooved portions of the two surfaces 20 abut or are closely adjacent each other and define the two channels 18, 18' as well as the slot 19' between them.

The means for shifting the sleeve 2 between the extended or first position of FIGS. 3 to 5 and the second position of FIGS. 1A, 1B includes a mechanism or linkage 21 which is shown in FIG. 1B. Such linkage includes a lug 21 at the rear end of the sleeve 2, a longer lug 23 spaced apart from the rear end of and affixed to the tube 1, a link 22a which is articulately connected to the lug 22, and a two-armed lever 24 which is fulcrumed on the lug 23, the shorter arm of which is articulately connected to the free end of the link 22a, and the longer arm of which can be manipulated by hand to move between the solid-line and broken-line positions of FIG. 1B. The sleeve 2 is retracted in response to pivoting of the lever 24 to the solid-line position, and the sleeve 2 is moved toward its second position in response to pivoting of the lever 24 to the broken-line position of FIG. 1B.

When the compartment 14 of the tube 1 receives two needles 16 and a length of thread 17, the lever 24 is pivoted to the broken-line position of FIG. 1B to thereby move the sleeve 2 to the first or locking position of FIGS. 3 and 4. The trough-shaped closure 5 is thereupon turned about the sleeve 2 so as to seal the inlet 25 of the sleeve, i.e., to confine the needles 16 and the thread 17 in the compartment 14.

The apparatus of FIGS. 1A to 5 preferably further comprises suitable sealing elements (not shown), e.g., in the form of O-rings. One or more such sealing elements can be interposed between the tube 1 and the sleeve 2 as well as between the tube 1 and the piston 4 and/or between the rear end of the tube 1 and the piston rod 3. The purpose of such sealing elements is to reduce the likelihood of a drop of pressure in the tube 1 when the jaws 9, 9' are introduced into an abdominal or thoracic cavity.

The operation of the apparatus of FIGS. 1 to 5 is as follows:

The first step involves the selection of appropriate matrices 12, 12' which are introduced into and releasably locked in the respective rails 11, 11' of the jaws 9, 9'. For example, the surgeon in charge will select matrices with smaller or larger teeth, depending on the nature of the organ which is to be clamped in the clearance 13 between the toothed surfaces 20 of the properly inserted matrices. The next step includes pivoting the lever 24 of the linkage 21 to the broken-line position of FIG. 1B so that the sleeve 2 is caused to move from the retracted position of FIG. 1A to the extended position of FIGS. 3, 4 and 5. Thus, the jaws 9, 9' are pivoted relative to each other about the respective bearing pins 8, 8' against the opposition of the respective torsion springs 10 and the jaws are thereupon locked in their closed positions. Thereafter, the knob 26 is grasped by hand to pull the piston 4 from the extended position (shown in FIG. 4) to the retracted position of FIG. 1A, namely behind the compartment 14. At such time, the inlet 25 of the sleeve 2 already registers with the inlet 15 of the tube 1 so that the empty compartment 14 is accessible for reception of two needles 16 and a looped length of thread 17 connecting the rear portions of the needles to each other. The closure 5 must be rotated to expose the inlet 25 of the sleeve 2 before the compartment 14 of the tube 1 can receive a length of thread 17 and two needles 16. The front portions of the two needles 16 are introduced into the passages 18 of the plug 6 before the closure is turned again to overlie the inlet 25 of the sleeve 2 and to thus prevent further access to the needles 16 and thread 17 in the compartment 14. The apparatus is then ready for introduction of the jaws 9, 9' (in closed positions) into a body cavity, e.g., through a customary trocar. As mentioned above, the body cavity can be an abdominal cavity or a thoracic cavity.

The jaws 9, 9' are permitted to move to open positions (under the bias of the springs 10 and in response to retraction of the sleeve 2 to the position of FIG. 1A) upon entry into a cavity. Thus, the lever 24 of the linkage is pivoted from the broken-line position to the solid-line position of FIG. 1B as soon as the jaws 9, 9' are free to pivot apart in the interior of an abdominal or thoracic cavity. The tube 1 is thereupon moved longitudinally relative to the trocar until the open jaws 9, 9' are properly located with reference to a selected portion of a viscus 27 in the cavity. Once the tube 1 assumes a desired or required position, the lever 24 of the linkage 21 is pivoted from the solid-line position to the broken-line position of FIG. 1B so that the jaws 9, 9' are compelled to pivot toward their closed positions and the selected portion of the viscus 27 is confined and clamped in the clearance 13 between the two toothed surfaces 20. The clamped portion of the viscus 27 is that portion which is to be traversed by the thread 17 in order to establish a seal similar to that at the openable end of a tobacco pouch.

Retraction of the piston rod 3, piston 4 and handle 26 to the positions of FIG. 1B is followed by the application of a locking device 51 in the form of a bolt insertable into a diametrically extending bore or hole of the piston rod 3. This ensures that the needles 16 are not accidentally moved out of the compartment 14 and into the channels 18' of the closed jaws 9, 9'. When the clamping of a selected portion of the viscus 27 in the clearance 13 between the matrices 12, 12' is completed, the person in charge extracts the locking device 51 from the bore of the piston rod 3 so that the handle 26 can be used to move the needles 16 and the thread 17 forwardly. The front ends of the needles penetrate through successive parts of the zig-zag shaped portion of the viscus 27 in the clearance 13, and the tips of the needles ultimately emerge from the channels 18' as shown in FIG. 4. The piston 4 is retracted immediately thereafter in order to avoid clamping of the thread 17 as well as to retract a cutter or knife, e.g., a cutter 31 which is shown in FIGS. 6 and 7, into the sleeve 2. FIG. 7 shows the sleeve 2 in a partly retracted position in which the sleeve permits coupling of the cutter 31 to a forwardly projecting extension 29 of the piston 4.

The front portions of the needles 16 are thereupon extracted in a forward direction (i.e., into the body cavity) by a tool 50 which is shown in FIG. 6. The extracting tool 50 can resemble a sardine can opener and the needles 16 are made of flexible, particularly ductile, material so that they can be rolled up into the shape of spirals (not specifically shown) in front of the closed jaws 9, 9'. The jaws are thereupon moved to their open positions under the action of the respective coil springs 10 and in response to pivoting of the lever 24 to the solid-line position of FIG. 1B, i.e., in response to retraction of the sleeve 2 at least to or even rearwardly beyond the plug 6 (see FIG. 1A). This separates the jaws 9, 9' from that deformed and stitched portion of the viscus 27 which was confined in the clearance 13 and was traversed first by the needles 16 and thereupon by portions of the thread 17. The needles 16 are separated from the thread 17 and the latter is tightened to contract the stitched portion of the viscus 27 in a manner known from the art of closing tobacco pouches. The surgeon thereupon resorts to a scalpel or to another cutter to sever the viscus 27 at a selected distance from the thread 17. However, it is presently preferred to equip the improved apparatus with the aforementioned cutter 31 which can be resorted to in order to sever the viscus 27 at a desired distance from the stitches of thread 17 which has been caused to pass through the viscus in response to extraction of the needles 16 by the tool 50. The cutter 31 renders it possible to simplify the cutting operation and to ensure that the viscus is invariably severed at a selected distance from the thread 17.

Referring now in detail to FIGS. 5 to 7, the plug 6 of the support for the jaws 9, 9' can be provided with an arcuate cutout 28 which can receive a complementary portion of the extension 29 forming part of the piston 4. The extension 29 passes into and in part beyond the cutout 28 when the piston 4 is moved forwardly relative to the plug 6. This extension is provided with an undercut female coupling portion 30 for reception of a complementary male coupling portion 32 on the cutter 31. FIG. 6 shows that a properly mounted cutter 31 is form-lockingly connected with the extension 29 of the piston 4. The front end of the cutter 31 is provided with a cutting edge 33 and has a segmental cross-sectional outline. When the cutter 31 is properly coupled to the device which serves to move the needles 16 out of the compartment 14, it shares the movements of the piston 4 relative to the tube 1 of the support for the jaws 9, 9'. During its movement relative to the jaws 9 and 9', the cutter 31 is guided by the sleeve 2 on the one hand and by the rails 11, 11' on the other hand.

The manner in which the cutter 31 can be coupled to or uncoupled from the piston 4 is shown in FIG. 7. Thus, the sleeve 2 must be retracted to expose the female coupling element 30 so that the latter can receive the male coupling element 32 or that the male coupling element can be withdrawn from the female coupling element.

When the cutter 31 is properly coupled to the piston 4, forward movement of the piston 4 to propel the needles 16 through the mutually inclined parts of that portion of a viscus 27 which is clamped between the matrices 12, 12' automatically results in severing of the viscus at a predetermined distance from the channels 18', i.e., at a fixed distance from the locus of subsequent penetration of the thread 17 through the viscus portion in the clearance 13. Such automatic severing or trimming of the viscus entails savings in time and ensures that the locus of cutting is disposed at a predetermined distance from the stitches of the thread 17.

Figure 9:
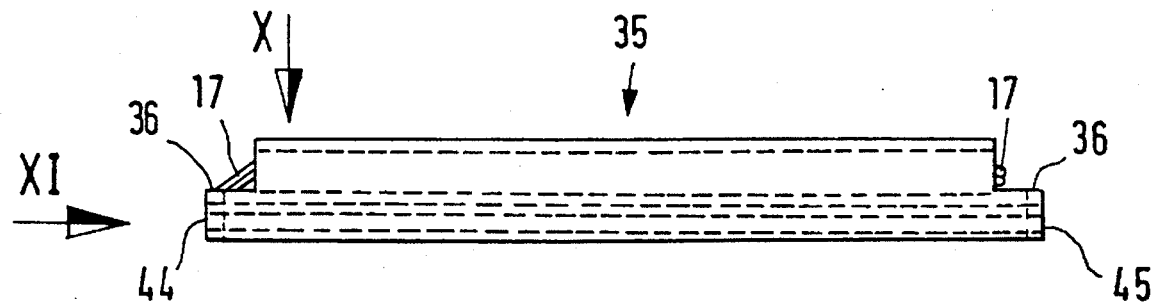
FIG. 9 is a side elevational view of a carriage for two needles which can be dropped or otherwise inserted into the compartment of the support in an apparatus or instrument of the type shown in FIGS. 1 through 7.
Figure 10:
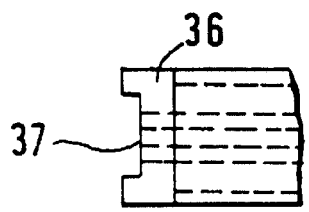
FIG. 10 is a fragmentary plan view of the carriage substantially as seen in the direction of arrow X in FIG. 9.
Figure 11:
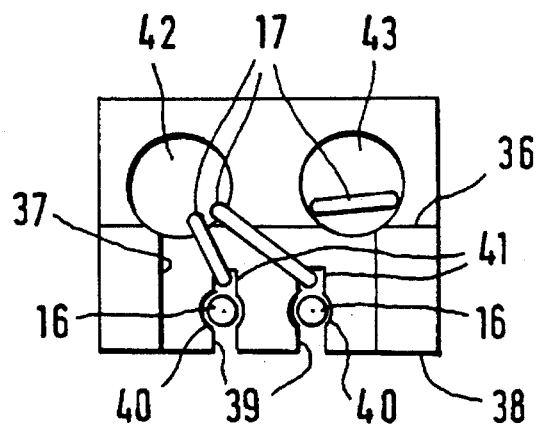
FIG. 11 is an enlarged end elevational view of the carriage, substantially as seen in the direction of arrow XI in FIG. 9.

Insertion of the needles 16 and thread 17 into the compartment 14 of the tube 1 must be carried out with utmost care in order to prevent the formation of knots or jamming of portions of the thread 17 prior to penetrating through the clamped portion of an organ. Jamming is particularly likely to take place while the piston 4 is moved forwardly to expel the needles 16 from the compartment 14, through the passages 18 of the plug 6 and into and beyond the channels 18' in the closed jaws 9, 9'. In order to simplify the task of the person in charge and to eliminate the likelihood of knotting or jamming of the thread 17 in the support for the jaws 9, 9' and/or during movement of the needles toward and beyond the positions of FIG. 4, it is proposed to employ a carriage 35 which can be of the type shown in FIGS. 9, 10 and 11. The utilization of such carriage simplifies the introduction of needles 16 into the compartment 14 and practically eliminates the likelihood of jamming, knotting and/or other undesirable influences upon the thread 17 whose ends are affixed to the rear portions of the needles. The illustrated carriage 35 is an elongated body which is or can be made of a suitable plastic material and preferably has a square, rectangular or other polygonal cross-sectional outline so that it can be snugly fitted into the compartment 14. The entire carriage 35 is properly sterilized and is expendable, i.e., it is preferably discarded after a single use.

The two ends 44, 45 of the carriage 35 are provided with transversely extending cutouts 36 and the end face of at least one of the ends 44, 45 is provided with a recess 37 extending at right angles to a plane external surface 38. The surface 38 is formed with two parallel longitudinally extending grooves 39 having enlarged portions 40 for reception of the needles 16. The innermost portions 41 of the grooves 39 constitute channels for reception of portions of the thread 17. The carriage 35 is further provided with two longitudinally extending chambers 42, 43 for confinement of portions of the thread 17. The ends of the chambers 42, 43 are located at the respective cutouts 36. The enlarged portions 40 of the grooves 39 are or can be disposed substantially midway between the external surface 38 and the thread-receiving channels 41. The dimensions of the chambers 42, 43 are or can be selected in such a way that they can confine the major portion of the thread 17.

In order to load the carriage 35 with two needles 16 and a length of thread 17, the rear ends of the needles are connected with the ends of the thread so that the thread forms a large loop between such rear ends. The rear ends of the needles 16 are thereupon introduced into the respective enlarged portions 40 of the grooves 39 in a direction from the first end 44 toward the second end 45 of the carriage. This causes two stretches of thread to advance in the channels 41 in the same direction, i.e., from the first end 44 toward the second end 45 of the carriage 35. A substantial (intermediate) portion of the thread 17 is then located at the first end 44, and such intermediate portion is moved through the chamber 42 from the end 44 toward the end 45 and thereupon into the chamber 43 in a direction from the end 45 toward the end 44. The advancement of thread 17 in the chamber 42 is preferably carried out in such a way that the bight of the loop which is formed by the intermediate portion of the thread between the front ends of the portions 41 is first to enter the channel 42 at the first end and to advance toward and beyond the second end of the chamber 42 at 45. The thread 17 which extends beyond the rear end of the chamber 42 forms a relatively small loop which can be readily confined in the chamber 43. Again, the bight of the relatively small loop of thread 17 at the rear end 45 of the carriage 35 is preferably first to enter the rear end of the chamber 43. The carriage 35 (with the two needles 16 and a requisite length of thread 17 in the portions 40, 41 of the grooves 39 and in the chambers 42, 43) is then ready to be dropped into the compartment 14 by way of the inlets 25 and 15 in the sleeve 2 and the tube 1, respectively. The first end 44 of the properly inserted carriage 35 is adjacent the plug 6 at the front end of the compartment 14. The dimensions of the carriage 35 are selected in such a way that, once the carriage is properly inserted into and confined in the compartment 14, the enlarged portions 40 of the grooves 39 automatically register with the adjacent rear ends of the passages 18 in the plug 6. Furthermore, the piston 4 is provided with two lobes (not specifically shown) which enter the grooves 39 at the second end 45 of the properly installed carriage 35 and push the rear ends of the needles 16 forwardly into the corresponding channels 18 of the plug 6. The lobes of the piston 4 are preferably dimensioned in such a way that they do not extend into the innermost portions 41 of the respective grooves 39 but reliably expel the needles 16 from the carriage 35 while the piston 4 is caused to advance along the external surface 38 of the carriage.

The purpose of the cutouts 36 and recesses 37 is to prevent jamming of thread 17 at the front end 44 of a carriage 35 which is properly installed in the compartment 14. It is preferred to make the first end 44 of the carriage 35 a mirror image of the second end 45. This ensures that the needles 16 and the thread 17 can be properly confined in the carriage irrespective of whether the rear ends of the needles are introduced into the respective enlarged portions 40 of the grooves 39 at the end 44 or at the end 45 of the carriage.

When the front ends of the needles 16 are thereupon extracted from the respective channels 18' by resorting to the tool 50 or to an analogous tool, the thread 17 between the rear ends of the needles can advance first through the slot 19 between the passages 18 in the plug 6 and thereupon through the composite slot 19' between the channels 18' of the jaws 9, 9' in the closed positions of the jaws. The thread 17 is thereupon separated from the needles 16 and is tightened around the viscus 27.

An advantage of the improved apparatus and of its cutter 31 is that a viscus can be trimmed at a selected distance from the sewn-together portion of the viscus which was clamped in the clearance 13.

An advantage of the support (including the tube 1 and the plug 6), of the pivotably mounted jaws 9, 9' and of the moving means (3, 4, 26, 50) for the needles 16 is that they contribute to simplicity of the apparatus and enable the surgeon to rapidly complete the treatment of a viscus.

The pivotably mounted jaws 9, 9' render it possible to utilize the improved apparatus for laparotomic surgery. This is in contrast to heretofore known apparatus which cannot be utilized for laparotomy. The sleeve 2 constitutes a simple but effective device for rapidly moving the jaws 9, 9' to their closed positions and for thereupon maintaining the jaws in closed positions as long as necessary. The provision of the aforedescribed moving means 3, 4, 26, 50 for the needles 16, and of the aforementioned linkage 21 to move the sleeve 2 relative to the tube 1, also contributes to the ability of the improved apparatus to find use in connection with laparotomic surgery.

The diameter of the sleeve 2 is preferably less than 19 millimeters. Thus, when the sleeve 2 is held in the position of FIGS. 3 to 5, the diameter of the apparatus in the region of the closed jaws 9, 9', plug 6 and sleeve 2 is sufficiently small to ensure convenient manipulation during introduction of the jaws into a body cavity and during subsequent manipulation of an organ in such cavity.

The aforedescribed two-piece jaws 9, 9' exhibit the advantage that they can accurately guide the thread 17 during tightening of thread around that portion of an organ which was previously held in the zig-zag shaped clearance 13 between the toothed surfaces 20 of the matrices 12 and 12'. Furthermore, such construction of the jaws 9 and 9' renders it possible to select appropriate matrices 12, 12' for a particular treatment, i.e., to properly select the number, the distribution and the dimensions of teeth which are to engage and clamp a selected portion of an organ in a body cavity.

The cutter 31 exhibits the aforediscussed advantages of ensuring that the severing of a clamped organ takes place at an optimum distance from the stitches of thread 17. This is desirable when a surgeon is to use the improved apparatus for resection in the course of laparotomic surgery. Moreover, the resection of an internal organ can be completed with little loss in time.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of our contribution to the art and, therefore, such adaptations should and are intended to be comprehended within the meaning and range of equivalence of the appended claims.

We claim:

1. Apparatus for clamping and sealing a viscus in a body cavity, comprising a support having a front end insertable into a body cavity, a rear end and a compartment disposed between said ends for receiving two needles having rear portions connected to each other by a length of flexible material and front portions; two jaws affixed and movable relative to said front end between closed positions in which a viscus is to be clamped therebetween and open positions, said jaws having channels each positioned to receive one of said needles from said compartment in closed positions of said jaws; and means for moving the needles from said compartment into and beyond said channels so that the needles entrain the flexible material from said compartment and through the viscus between said jaws;

wherein said support includes an elongated tube and said compartment is disposed in said tube at the front end of said support; and wherein said moving means includes a piston reciprocable in said tube toward and away from said front end to expel the needles from said compartment into said channels in response to movement toward said front end and in closed positions of said jaws.

2. The apparatus of claim 1, further comprising said length of flexible material for connection of the two needles, wherein said flexible material includes a length of thread and said channels communicate with each other in the closed positions of said jaws so that a looped portion of the thread between the rear portions of the needles can be tightened against a viscus between said jaws in response to movement of said needles beyond said channels and into a body cavity.

3. The apparatus of claim 1, wherein said tube has an inlet for introduction of needles into said compartment.

4. The apparatus of claim 1, wherein said piston is movable away from said front end toward said rear end to a position beyond said compartment so that the compartment is free to receive two needles.

5. The apparatus of claim 1, wherein said tube has a longitudinal axis and said jaws are substantially mirror images of each other with reference to a plane including said axis, said channels being at least substantially parallel to said axis in the closed positions of said jaws and said front end of said support having interconnected centering passages aligned with said channels and communicatively connecting said channels with said compartment in the closed positions of said jaws.

6. The apparatus of claim 1, wherein said support has a longitudinal axis and said jaws are pivotable relative to said front end about substantially parallel axes which are at least substantially normal to said longitudinal axis.

7. The apparatus of claim 6, wherein said support has a first external surface and said jaws have second external surfaces at least substantially flush with portions of said first external surface in the closed positions of said jaws.

8. The apparatus of claim 7, further comprising a sleeve surrounding a portion of said support and movable in the direction of said axis between a first position in which the sleeve surrounds at least a portion of each of said jaws in the closed positions of the jaws and a second position in which the jaws are free to pivot relative to said front end toward and from said open positions.

9. The apparatus of claim 1, further comprising means for biasing said jaws to said open positions.

10. The apparatus of claim 1, further comprising a sleeve surrounding a portion of said support and movable relative to said support between a first position in which the sleeve surrounds at least a portion of each of said jaws in the closed positions of the jaws and a second position in which the jaws are free to move toward and from the open positions thereof, and a linkage carried by said support and operatively connected with said sleeve, said linkage being actuatable to move said sleeve between the first and second positions thereof.

11. The apparatus of claim 1, further comprising a sleeve surrounding a portion of said support and movable relative to said support between a fist position in which the sleeve surrounds at least a portion of each jaw in the closed positions of the jaws and a second position in which the jaws are free to move toward and from their open positions, said sleeve having an outer diameter less than 19 millimeters.

12. The apparatus of claim 1, wherein said jaws have confronting teeth defining a zig-zag shaped clearance in the closed positions of said jaws.

13. The apparatus of claim 1, further comprising a cutter substantially parallel with said jaws in the closed positions of the jaws and movable relative to the closed jaws to sever a viscus which is being clamped by said jaws.

14. The apparatus of claim 13, further comprising means for coupling said cutter with said moving means so that the cutter is moved relative to the closed jaws in response to movement of said needles from said compartment into and beyond said channels.

15. Apparatus for clamping and sealing a viscus in a body cavity, comprising a support having a front end insertable into a body cavity, a rear end and a compartment disposed between said ends for receiving two needles having rear portions connected to each other by a length of flexible material and front portions; two jaws affixed and movable relative to said front end between closed positions in which a viscus is to be clamped therebetween and open positions, said jaws having channels each positioned to receive one of said needles from said compartment in closed positions of said jaws; and means for moving the needles from said compartment into and beyond said channels so that the needles entrain the flexible material from said compartment and through the viscus between said jaws;

wherein said support includes an elongated tube and said compartment is disposed in said tube at the front end of said support;

wherein said tube has a longitudinal axis and said jaws are substantially mirror images of each other with reference to a plane including said axis, said channels being at least substantially parallel to said axis in the closed positions of said jaws and said front end of said support having interconnected centering passages aligned with said channels and communicatively connecting said channels with said compartment in the closed positions of said jaws; and wherein said passages are holes in the front end of said support and said front end has a slot between said holes.

16. Apparatus for clamping and sealing a viscus in a body cavity, comprising a support having a front end insertable into a body cavity, a rear end and a compartment disposed between said ends for receiving two needles having rear portions connected to each other by a length of flexible material and front portions; two jaws affixed and movable relative to said front end between closed positions in which a viscus is to be clamped therebetween and open positions, said jaws having channels each positioned to receive one of said needles from said compartment in closed positions of said jaws; and means for moving the needles from said compartment into and beyond said channels so that the needles entrain the flexible material from said compartment and through the viscus between said jaws; and wherein said support has a first inlet for admission of needles into said compartment and further comprising a sleeve surrounding a portion of said support and movable with reference to said support between a first position in which said sleeve surrounds at least a portion of each of said jaws in the closed positions of the jaws and a second position in which the jaws are free to move toward and from open positions, said sleeve having a second inlet which registers with said first inlet at least in the first position of said sleeve.

17. Apparatus for clamping and sealing a viscus in a body cavity, comprising a support having a front end insertable into a body cavity, a rear end and a compartment disposed between said ends for receiving two needles having rear portions connected to each other by a length of flexible material and front portions; two jaws affixed and movable relative to said front end between closed positions in which a viscus is to be clamped therebetween and open positions, said jaws having channels each positioned to receive one of said needles from said compartment in closed positions of said jaws; and means for moving the needles from said compartment into and beyond said channels so that the needles entrain the flexible material from said compartment and through the viscus between said jaws; and wherein said support includes an elongated cylinder and said moving means comprises a piston reciprocable in said cylinder, and having a piston rod extending from said cylinder beyond the rear end of said support.

18. The apparatus of claim 17, wherein said moving means further comprises a handle provided on said piston rod externally of said cylinder.

19. The apparatus of claim 1, wherein each of said jaws comprises a first portion movably affixed to said support and a second portion engageable with a viscus and detachably carried by the respective first portion.

20. The apparatus of claim 19, wherein each of said first portions includes an elongated rail and each of said second portions includes an elongated toothed matrix releasably secured to the respective rail.

21. Apparatus for clamping and sealing a viscus in a body cavity, comprising a support having a front end insertable into a body cavity, a rear end and a compartment disposed between said ends for receiving two needles having rear portions connected to each other by a length of flexible material and front portions; two jaws affixed and movable relative to said front end between closed positions in which a viscus is to be clamped therebetween and open positions, said jaws having channels each positioned to receive one of said needles from said compartment in closed positions of said jaws; and means for moving the needles from said compartment into and beyond said channels so that the needles entrain the flexible material from said compartment and through the viscus between said jaws;

wherein the apparatus further comprises
a cutter substantially parallel with said jaws in the closed positions of the jaws and movable relative to the closed jaws to sever a viscus which is being clamped by said jaws;
means for coupling said cutter with said moving means so that the cutter is moved relative to the closed jaws in response to movement of said needles from said compartment into and beyond said channels; and
wherein said moving means includes a piston which is reciprocable in said support, said coupling means including an extension provided on said piston, projecting toward said jaws and connectable with a portion of said cutter.

22. The apparatus of claim 21, wherein said first end has centering passages communicating with said compartment and aligned with said channels in the closed positions of said jaws to establish a path for movement of needles from said compartment into said channels in the closed positions of the jaws, said extension projecting beyond and being adjacent said passages in response to movement of said needles at least partly beyond said channels.

23. Apparatus for clamping and sealing a viscus in a body cavity, comprising a support having a front end insertable into a body cavity, a rear end and a compartment disposed between said ends for receiving two needles having rear portions connected to each other by a length of flexible material and front portions; two jaws affixed and movable relative to said front end between closed positions in which a viscus is to be clamped therebetween and open positions, said jaws having channels each positioned to receive one of said needles from said compartment in closed positions of said jaws; and means for moving the needles from said compartment into and beyond said channels so that the needles entrain the flexible material from said compartment and through the viscus between said jaws; and wherein said moving means comprises means for extracting the needles from the channels into a body cavity in closed positions of said jaws.

24. The apparatus of claim 23, wherein said extracting means comprises means for converting the needles into spirals.

25. The apparatus of claim 24, further comprising the two needles, wherein the needles contain a ductile material.

26. As a novel article of manufacture for use with a surgical apparatus for clamping and sealing a viscus wherein a support has an end mounting two jaws for movement between open and closed positions, wherein a sleeve surrounds a portion of and is movable relative to the support to and from a predetermined position in which the sleeve at least partially surrounds the jaws in the closed positions thereof, and wherein a device is provided to move two needles from a compartment in the support into and beyond channels provided in the jaws;

wherein said support includes an elongated tube and said compartment is disposed in said tube at the front end of said support;
wherein said moving means includes a piston reciprocable in said tube toward and away from said front end to expel the needles from said compartment into said channels in response to movement toward said front end and in closed positions of said jaws; and
the article comprises a cutter having a portion connectable with said device for movement relative to and between the sleeve and the jaws in the closed positions of the jaws and in the predetermined position of the sleeve.

27. As a novel article of manufacture for use in a surgical apparatus for clamping and sealing a viscus, the article comprising a support having an elongated compartment, an elongated carriage insertable into and withdrawable from the compartment, the compartment having an external surface provided with two longitudinally extending needle-confining grooves, said carriage further having two longitudinally extending thread-receiving channels each communicating with one of said grooves and at least one longitudinally extending thread-receiving chamber having at least one open end; and wherein said clamping of the viscus is effected in a direction transverse to a longitudinal direction of said support, and said needle-confining grooves extend in said longitudinal direction for directing needles in said longitudinal direction upon engagement of said needles with the viscus.

28. The carriage of claim 27, further having a first end and a second end and a recess at one of said ends, said grooves and said channels having ends in communication with said recess.

29. The carriage of claim 28, further having a cutout at one of said ends, said at least one open end of said at least one chamber communicating with said cutout.

30. The apparatus of claim 28, wherein said ends are mirror images of each other.

31. A needle moving device operative with an apparatus for clamping and sealing a viscus in a body cavity, wherein the apparatus comprises a support having a front end insertable into the body cavity, a rear end and a compartment disposed between said front end and said rear end for securing two needles each of which has a front portion and a rear portion, wherein the rear portions of the needles are connected to each other by a length of flexible material;

the apparatus further comprises two jaws affixed to the front end of said support and being movable relative to the support between a closed position wherein the viscus is to be clamped by the jaws and an open position, said jaws having channels for receiving respective ones of said needles from said compartment in the closed position of said jaws;

the apparatus further comprises means for advancing the needles from the compartment via said channels to entrain the needles within a portion of the viscus held by said jaws; and wherein the moving device comprises means for extracting the needles from the channels into the body cavity in the closed position of said jaws, the extracting being

* * * * *